United States Patent
Tkaczyk et al.

(10) Patent No.: US 8,160,200 B2
(45) Date of Patent: Apr. 17, 2012

(54) METHOD AND SYSTEM FOR IMAGE DATA ACQUISITION

(75) Inventors: John Eric Tkaczyk, Delanson, NY (US); David Allen Langan, Clifton Park, NY (US); Samit Kumar Basu, Newark, CA (US); Xiaoye Wu, Rexford, NY (US); Bruno Kristiaan Bernard De Man, Clifton Park, NY (US); Jeffrey Seymour Gordon, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 198 days.

(21) Appl. No.: 12/750,050

(22) Filed: Mar. 30, 2010

(65) Prior Publication Data

US 2011/0243413 A1    Oct. 6, 2011

(51) Int. Cl.
*H05G 1/26* (2006.01)

(52) U.S. Cl. .............................. 378/19; 378/4

(58) Field of Classification Search ................ 378/4–20, 378/114–116, 207
See application file for complete search history.

(56) References Cited

U.S. PATENT DOCUMENTS

| | | | |
|---|---|---|---|
| 6,759,658 | B2 | 7/2004 | Overdick et al. |
| 7,551,708 | B2 | 6/2009 | Basu et al. |
| 2007/0076842 | A1* | 4/2007 | Tkaczyk et al. .................. 378/5 |
| 2007/0147574 | A1 | 6/2007 | De Man et al. |
| 2007/0165771 | A1* | 7/2007 | Haras et al. ........................ 378/4 |
| 2008/0001095 | A1 | 1/2008 | Astley et al. |
| 2008/0240341 | A1 | 10/2008 | Possin et al. |

FOREIGN PATENT DOCUMENTS

| | | |
|---|---|---|
| EP | 492895 A2 | 7/1992 |
| EP | 1876955 A2 | 1/2008 |
| WO | 2006114715 A2 | 11/2006 |
| WO | 2009120417 A1 | 10/2009 |

OTHER PUBLICATIONS

B. J. Heismann and S. Wirth; "SNR performance comparison of Dual-Layer Detector and Dual-kVp spectral CT"; 1-4244-0923-3/07/$25.00 © 2007 IEEE; 3 Pages.

Salvatore Lanzavecchia, Pier Luigi Bellon and Michael Radermacher; "Fast and Accurate Three-Dimensional Reconstruction From Projections With Random Orientations Via Radon Transforms"; Received May 31, 1999;revised Sep. 3, 1999.Available online Mar. 27, 2002; Abstract found in 5th Page.

Search Report from corresponding EP Application No. 11159253.1-2319 dated Aug. 30, 2011.

* cited by examiner

*Primary Examiner* — Hoon Song
(74) *Attorney, Agent, or Firm* — Jason K. Klindtworth

(57) ABSTRACT

A technique for acquiring desired image data in an imaging system comprising at least one radiation source and a detector is described. Initially, preliminary image data corresponding to an object may be acquired. Further, at least one parameter associated with the radiation source and corresponding to a particular view angle of the radiation source may be determined based on the preliminary image data and a priori information. Similarly, at least one parameter associated with the detector and corresponding to the particular view angle may be determined based on a priori information and the preliminary image data. Efficient operating modes of the radiation source and the detector corresponding to the particular view angle may be selected based on the determined parameters to achieve a desired system performance. Subsequently, the final image data may be acquired using the selected operating modes of the radiation source and the detector.

33 Claims, 4 Drawing Sheets

METHOD AND SYSTEM FOR IMAGE DATA ACQUISITION

BACKGROUND

Embodiments of the present technique relate generally to diagnostic imaging, and more particularly to a technique for adaptive configuration of a source and a detector in an imaging system for optimal data acquisition.

Radiographic imaging systems typically include a radiation source that emits radiation towards an object, such as a patient or a piece of luggage. A radiation beam, after being attenuated by the object, impinges upon an array of radiation detectors. Generally, the radiation beam intensity received at the detector array depends upon the attenuation of the radiation beam through the scanned object. Particularly, each detector in the detector array generates a separate signal indicative of the attenuated beam received by the detector. Subsequently, each detector transmits the generated signal to a data processing system for analysis and further processing to facilitate image reconstruction.

Conventionally, radiation detectors are employed in emission imaging systems, for example, nuclear medicine (NM) gamma cameras, computed tomography (CT) systems and positron emission tomography (PET) systems. Typically, the CT systems include an X-ray source and a detector array that are rotated about a gantry encompassing an imaging volume around the object. Particularly, the detector array in the CT systems employs detectors that convert X-ray photon energy into current signals that are integrated over a time period, then measured, and ultimately digitized. Furthermore, the CT imaging systems typically include photon-counting (PC) detectors that provide dose efficient X-ray spectral information, energy discrimination and material decomposition capabilities. Conventional PC detectors, however, are subject to saturation effects at high X-ray flux, for example, at or above 5-100 million counts per sec per millimeter squared (Mcps), due to pile-up and polarization. Detector saturation causes loss of imaging information, thereby resulting in severe artifacts in reconstructed X-ray projection and CT images. Some CT systems, therefore, employ energy integrating (EI) detectors that do not experience saturation at high X-ray flux rates. These EI detectors, however, provide only limited energy information. Additionally, at low flux rates, these EI detectors suffer from electronic noise.

Accordingly, recent detectors have been designed to provide either or both of photon counting and energy discriminating feedback. These types of detectors, however, still have limited count rates. Moreover, these detectors may not cover broad dynamic ranges encompassing very high X-ray photon flux rates typically encountered with conventional CT systems, where the very high X-ray photon flux rates ultimately lead to detector saturation.

Several techniques have been proposed to address detector saturation. These techniques include simultaneous readout of PC and EI data so that EI data is always available in regions where the PC data is saturated and PC data is available in regions where the flux is small. Although these simultaneous readouts solve the problem of saturated regions by providing EI data, these techniques fail to provide energy information in the saturated regions. Accordingly, alternative techniques have been designed to employ a predictive algorithm for configuring a desired detector setting for acquiring imaging data in different regions. It is however noted that actuation of the predictive algorithm may be regional on the detector making it difficult to select a setting (PC or EI) that works for neighboring regions.

A particularly challenging task is to configure detector settings for imaging coronary vessels in a lung field. As the lung field is adjacent to the coronary vessels and the sternum, high flux and low flux regions are proximally positioned and are encountered at the detector in rapid succession in time. Accordingly, switching a detector from a PC mode to an EI mode in conventional imaging systems may not be fast enough to allow acquisition of sufficient data for an efficient image reconstruction which, in turn, may affect accuracy of a diagnosis.

It would therefore be desirable to design a method and a system that overcome flux rate limitations of conventional detectors and organize acquisition of sufficient data for different system configurations to reconstruct a high quality image. Additionally, there is a need for a system that provides faster scanning and efficient material discrimination capability even with lower doses of radiation.

BRIEF DESCRIPTION

In accordance with aspects of the present technique, a method for acquiring desired image data in an imaging system comprising at least one radiation source and a detector is presented. Preliminary image data corresponding to at least a portion of an object may be acquired. Further, at least one parameter associated with the radiation source and corresponding to a particular view angle of the radiation source may be determined based on the preliminary image data and a priori information. Similarly, at least one parameter associated with the detector and corresponding to the particular view angle of the radiation source may be determined based on a priori information and the preliminary image data. Subsequently, an operating mode of the radiation source corresponding to the particular view angle may be selected based on the determined parameter corresponding to the radiation source to achieve a desired system performance. Similarly, an operating mode of the detector corresponding to the particular view angle may be selected based on the determined parameter corresponding to the detector to achieve the desired system performance. Subsequently, the final image data may be acquired using the selected operating modes of the radiation source and the detector.

In accordance with another aspect of the present technique, an imaging system is described. The imaging system may include at least one radiation source that emits radiation towards an object and a detector that receives the radiation from the radiation source. The imaging system may further include a data acquisition system (DAS) that acquires preliminary image data corresponding to at least a portion of the object. The DAS may determine at least one parameter associated with the radiation source and corresponding to a view angle of the radiation source based on one or more of the a priori information, and the preliminary image data. Similarly, the DAS may also determine at least one parameter associated with the detector and corresponding to the view angle of the radiation source based on at least one of the a priori information, and the preliminary image data. The imaging system may further include an adaptive controller for selecting an operating mode of the radiation source and an operating mode of the detector corresponding to the view angle of the radiation source. The adaptive controller may make the selection based on the determined parameters associated with the radiation source and the detector to achieve a desired system performance.

In accordance with a further aspect of the present technique, a computer tomography (CT) system is disclosed. The CT system may include a rotatable gantry having an opening to receive an object to be scanned. The CT system may also include at least one radiation source coupled to the gantry, such that the radiation source emits radiation towards the object. The CT system may further include a detector that receives the radiation from the radiation source. Additionally, the CT system may include a computing device that may acquire preliminary image data corresponding to at least a portion of an object. The computing device may determine at least one parameter associated with the radiation source corresponding to a view angle of the radiation source based on a priori information, the preliminary image data, or a combination thereof. Similarly, the computing device may also determine at least one parameter associated with the detector corresponding to the view angle of the radiation source and based on the a priori information, the preliminary image data, or a combination thereof. Further, the computing device may select an operating mode of the radiation source and an operating mode of the detector corresponding to the view angle of the radiation source. Particularly, the computing device may select the operating modes based on the determined parameters associated with the radiation source and the detector to achieve a desired system performance. Subsequently, the computing device may acquire final image data corresponding to at least portion of the object using the selected operating mode of the radiation source and the selected operating mode of the detector.

DRAWINGS

These and other features, aspects, and advantages of the present technique will become better understood when the following detailed description is read with reference to the accompanying drawings in which like characters represent like parts throughout the drawings, wherein.

DETAILED DESCRIPTION

The following description presents a technique for adaptive configuration of a source and a detector in an imaging system for acquiring image data corresponding to an object of interest. Particularly, embodiments illustrated hereinafter disclose an imaging system, such as a computed tomography (CT) system, and a method for acquiring image data for enhanced image reconstruction. Although exemplary embodiments of the present technique are described in the context of a CT system, it will be appreciated that use of the present technique in various other imaging applications and systems is also contemplated. Some of these systems may include a positron emission tomography (PET) scanner, a multiple source imaging system, a multiple detector imaging system, a single photon emission computed tomography (SPECT) scanner, microscopes, digital cameras, charge coupled devices, or combinations thereof. An exemplary environment that is suitable for practicing various implementations of the present technique is discussed in the following sections with reference to FIGS. 1-2.

Figure 1:
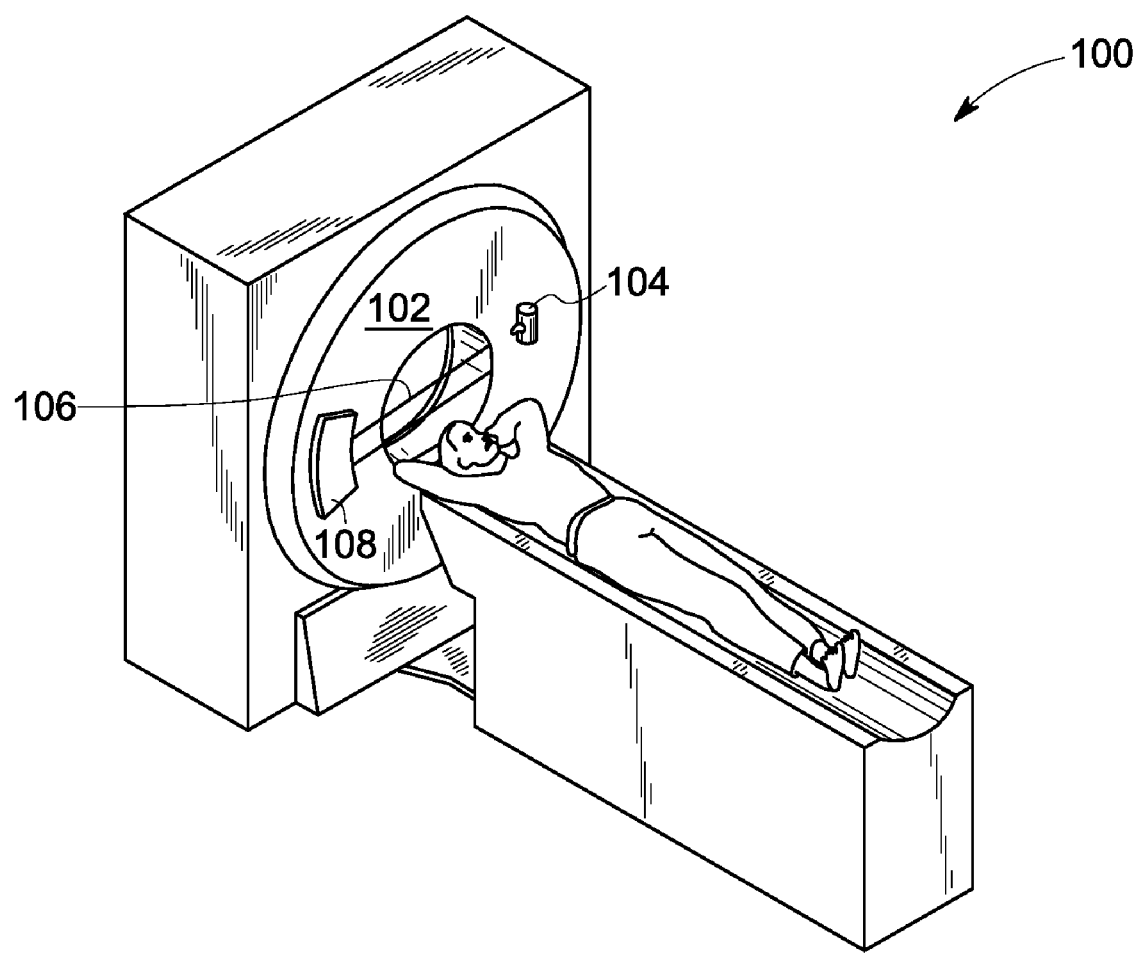
FIG. 1 is a pictorial view of a CT imaging system.
Figure 2:
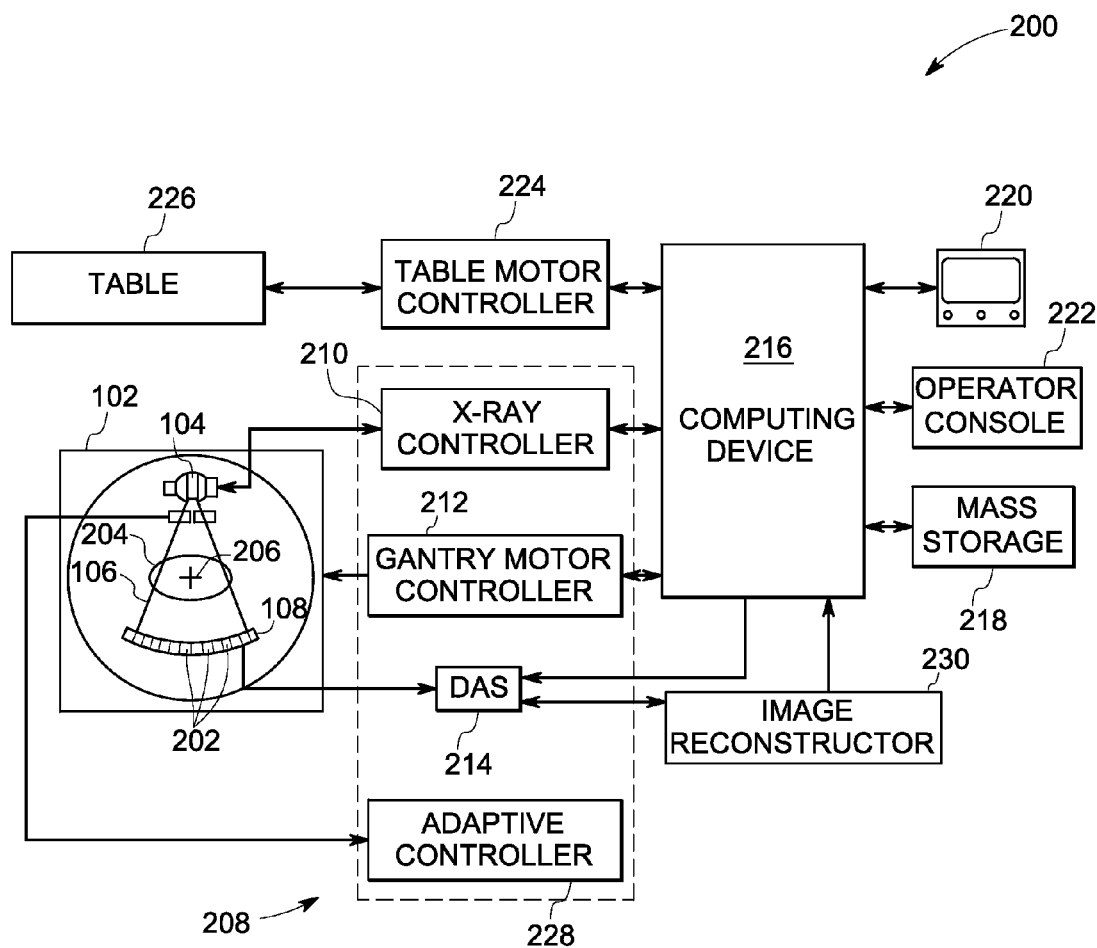
FIG. 2 is a block schematic diagram of the CT imaging system illustrated in FIG. 1 including an exemplary adaptive controller, in accordance with aspects of the present technique.

FIG. 1 illustrates an exemplary imaging system 100 for acquiring and processing image data. In one embodiment, the imaging system 100 may be a CT system including a gantry 102. The gantry 102 may include at least one X-ray radiation source 104 that projects a beam of X-ray radiation 106 towards a detector array 108 positioned on the opposite side of the gantry 102. The X-ray beam 106 may be, for example, a fan beam, a cone beam, or a parallel beam. In some embodiments, multiple radiation sources may be employed to project a plurality of X-ray beams for acquiring image data from different view angles. Further, FIG. 2 illustrates a CT imaging system 200, similar to the imaging system 100 of FIG. 1, for acquiring and processing image data in accordance with aspects of the present technique. The CT imaging system 200, however, may differ from the imaging system 100 in one or more structural and functional aspects. By way of example, the detector array 108 of the CT imaging system 200 may further include a plurality of detector elements 202 that together sense the projected X-ray beams that pass through an object 204, such as a medical patient or a baggage. Each of the detector elements 202 may produce an electrical signal that represents the intensity of the impinging X-ray beam 106, which may be used to estimate the attenuation of the X-ray beam 106 as it passes through the object 204. In some embodiments, the detector array 108 may be fabricated in a multi-slice configuration that may include a plurality of rows of cells or detector elements 202. In such a configuration, one or more additional rows of the detector elements 202 may typically be arranged in a parallel configuration for acquiring projection data.

Further, during a scan to acquire the projection data, the gantry 102 and the components mounted thereon may rotate about a center of rotation 206. However, in certain embodiments where a projection angle relative to the imaged object 204 varies as a function of time, the mounted components may move along a general curve rather than along a segment of a circle. Accordingly, the rotation of the gantry 102 and the operation of the X-ray source 104 may be controlled by a control mechanism 208 of the system 200 to acquire projection data from a desired view angle of the X-ray source 104. In one embodiment, the control mechanism 208 may include an X-ray controller 210 that provides power and timing signals to the X-ray source 104 and a gantry motor controller 212 that controls the rotational speed and position of the gantry 102. The control mechanism 208 may also include a data acquisition system (DAS) 214 for sampling analog data from the detector elements 202 and converting the analog data to digital signals for subsequent processing.

The data sampled and digitized by the DAS 214 may be input to a computer 216. The computer 216 may store this data in a mass storage 218 or in other storage media, such as, a floppy disk drive, a compact disk-read/write (CD-R/W) drive, or a Digital Versatile Disc (DVD) drive. The storage media may be used for reading and writing the sampled and digitized data onto removable media such as a floppy disk, a compact disk, or a DVD. These devices and storage media, in one embodiment, may be used to transfer the acquired projection data from the system 200 to other devices that are communicatively coupled to the computer 216 over a communications network for further processing. Alternatively, the devices and storage media may be used to input machine-readable instructions that may be processed by the computer 216.

Further, a display 220 may be communicatively coupled to the computer 216 to allow an operator to observe object images and related data. In one embodiment, the computer 216 may receive commands and scanning parameters from the operator via a console 222 that may include a keyboard (not shown). The computer 216 may use the operator supplied or system defined commands and parameters to provide control signals and information to one or more of the DAS 214, the X-ray controller 210 and the gantry motor controller 212. Additionally, the computer 216 may also operate a conveyor system controller or a table motor controller 224 that, in turn, controls a conveyor system or a motorized table 226. The table motor controller 224 may move the motorized table 226 for appropriately positioning the object 204, such as the patient, in the gantry 102 to acquire corresponding preliminary image data. The preliminary image data may include, for example, object parameters such as object structure, thickness, eccentricity, density, mass, or combinations thereof. The preliminary image data may further include system parameters such as the pile up behavior of the detector elements 202 and one or more operating parameters associated with either or both of the radiation source 104 and the detector elements 202.

Particularly, the one or more operating parameters associated with the radiation source 104 may include a view angle, a current configuration (mA), a voltage configuration (kVp), a time configuration, or combinations thereof. Similarly, the one or more operating parameters associated with the detector elements 202 may include a count of corresponding energy bins, a corresponding energy bin threshold, a pile-up behavior of the detector elements 202, a determined flux in the detector elements 202 corresponding to a particular view angle of the radiation source 104, or combinations thereof. In accordance with aspects of the present technique, the computer 216 may determine desired operating parameters associated with the radiation source 104 and the detector elements 202 based on the acquired preliminary image data. The computer 216 may further utilize a priori information while determining the desired parameters.

The a priori information may include determined information such as a correlation between one or more previously determined parameters associated with the radiation source 104 and the detector elements 202 corresponding to a particular view angle of the X-ray source 104. By way of example, the a priori information may include a correlation between a determined flux rate in the detector elements 202 corresponding to a particular view angle of the radiation source 104 and the mA and the kVp corresponding to the radiation source 104. Alternatively, the a priori information may also include preliminary image data and any information about the scanned object 204 acquired before the CT scan or input by the user through the operator console 222. By way of example, a scout scan may establish an object size, an object shape and an object density profile. The preliminary image data acquired from the scout scan may be used to estimate a flux rate in the detector elements 202 corresponding to a particular view angle and the mA and kVp corresponding to the X-ray source 104.

Additionally, the computer 216, thus, may use the acquired preliminary image data along with the a priori information to control an acquisition sequence and a plurality of flux level profiles corresponding to the imaging system 200. By way of example, in one embodiment, the computer 216 may select a high kVp and a high mA as desired optimal operating parameters of the radiation source 104 for acquiring image data corresponding to a relatively thick portion of the object 204. Alternatively, the computer 216 may select a low kVp and a low mA as the optimal operating parameters of the radiation source 104 for acquiring image data corresponding to a relatively thin portion of the object 204. As used herein, the term "thick portion of the object" refers to a portion of the object 204 that causes relatively heavy attenuation of the X-ray beam 106 and corresponding X-ray flux as it passes through the object 204 as compared to other portions of the object 204. In one embodiment, the attenuation caused by the thick portion may approximately be a factor of exp (−0.2*T), where exp is an exponential function and T is a thickness equivalent of water measured in centimeters. By way of example, the thick portion may be representative of a portion having greater than 20-25 cm equivalent attenuation of water and may be characterized by a flux attenuation of about 98-99% where less than 1-2% of the flux incident to the object 204 reaches the detector 108. Similarly, as used herein, the term "thin portion" of the object refers to a portion of the object 204 that causes relatively less attenuation of the X-ray beam 106 as it passes through the object 204 as compared to other portions of the object 204. By way of example, the thin portion may be representative of a portion having equivalent attenuation of water less than 15-20 cm and may be characterized by a flux attenuation of about 95-98% where only about 2-5% of the flux incident to the object 204 reaches the detector 108.

Further, in some embodiments, multiple radiation sources may be employed to illuminate different portions of the object 204. To that end, the computer 216 may operate each of the multiple radiation sources independently at a different mA to implement a virtual bowtie filter. The virtual bowtie filter may be used to shape the flux incident on the object 204 such that the portions of the object 204 that require higher signal-to-noise ratio (SNR) may receive higher flux. Typically, the center of the object 204 may be thicker as compared to other portions of the object 204 and thus, may require higher SNR for efficient data acquisition. Therefore, in one embodiment, the virtual bowtie filter may shape the flux such that there is more flux towards the center of the object 204 and less flux towards an edge of the object 204. Moreover, the computer 216 may independently configure the multiple radiation sources to acquire overlapping views of the different portions of the object 204 to provide sufficient information to reconstruct a high quality CT image.

In addition, the computer 216 may also determine a desired operating mode of the detector elements 202 based on the acquired preliminary image data and the a priori information. Particularly, the computer 216 may determine an X-ray flux in the detector elements 202 corresponding to a particular view angle of the radiation source 104. Typically, high X-ray flux may be observed at detector elements 202 where portions of the object 204 having a relatively small thickness are interposed between the detector elements 202 and the radiation source 104. Alternatively, lower X-ray flux may be observed at the detector elements 202 corresponding to relatively thicker portions of the object 204. As previously noted, the detector elements 202 operating in the photon counting (PC) mode may experience saturation at high X-ray flux, whereas the detector elements 202 operating in the energy-integrating (EI) mode may experience electronic noise at low X-ray flux. The computer 216, therefore, may switch one or more of the detector elements 202 between a PC mode, an EI mode, or a combination thereof, based on the determined flux to achieve a desired system performance.

However, in accordance with certain further aspects of the present technique, the system 200 may include an adaptive controller 228 for selecting desired operating modes of the radiation source 104 and the detector elements 202 corresponding to the particular view angle of the radiation source 104. Particularly, the adaptive controller 228 may select the desired operating modes based on determined parameters associated with the radiation source 104 and the detector elements 202. In such embodiments, the computing device 216 may not perform the step of selecting the desired operating modes of the radiation source 104 and the detector elements 202. Instead, the adaptive controller 228 may perform the selection. The adaptive controller 228 may further switch the radiation source 104 and one or more of the detector elements 202 between the selected operating modes to achieve a desired system performance. To that end, the adaptive controller 228 may include additional circuitry, such as a switching interface, for switching the radiation source 104 and one or more of the detector elements 202 between the selected operating modes. Alternatively, the adaptive controller 228 may transmit digital signals to the X-ray controller 210 and DAS 214 for switching the radiation source 104 and one or more of the detector elements 202 between the selected operating modes.

By way of example, the adaptive controller 228 may use the switching interface to perform fast switching of the radiation source 104 between a high kVp, a low kVp, a high mA, a low mA, or combinations thereof, to acquire projection data for efficient image reconstruction. In one embodiment, fast switching of the radiation source 104 may occur on a view-by-view basis and may typically be in the order of 1/10 of a view period. In certain embodiments, the fast switching of the radiation source 104 may be in the order of 0.2-2 milliseconds. Further, the adaptive controller 228 may switch the radiation source 104 alternately between a high kVp and a low kVp. In one embodiment, the adaptive controller 228 may perform the switch such that each high kVp view is followed by two adjacent low kVp views. Particularly, the adaptive controller 228 may select the operating mode of the detector elements 202 such that the flux in the detector elements 202 corresponds to a high detector quantum efficiency (DQE) operation in a PC mode for acquiring image data from a relatively highly attenuating portion of the object 204. To that end, the adaptive controller 228 may determine a flux in the detector elements 202 corresponding to the particular view angle of the radiation source 104. Further, the adaptive controller 228 may also switch one or more of the detector elements 202 between the PC mode and the EI mode based on the determined flux to acquire final image data.

Subsequently, the DAS 214 may acquire desired image data corresponding to at least a portion of the object 204 by employing the selected operating mode of the radiation source 104 and the detector elements 202. In accordance with aspects of the present technique, the final image data along with the preliminary image data and the a priori information may be communicated to an image reconstructor 230. The image reconstructor 230 may further receive information relating to one or more criteria employed as the basis for selecting the desired operating modes of the radiation source 104 and the detector elements 202, for example, from the computing device 216. Further, the image reconstructor 230 may employ the information corresponding to the one or more criteria for reconstructing a basis set image of the object 204 based on the final image data. To that end, the image reconstructor 230 may perform material decomposition of at least the portion of the object 204 based on the a priori information, the preliminary image data, the determined parameters of the radiation source 104 and the detector elements 202, and the selected operating mode of the radiation source 104 and the detector elements 202. The image reconstructor 230 may further process the final image data to achieve the desired system performance, thereby generating processed image data. Subsequently, the image reconstructor 230 may reconstruct a high quality image of the object 204 based on the processed image data. An exemplary method for configuring the radiation source 104 and the detector elements 202 to acquire desired image data for reconstructing the high quality image will be described in greater detail with reference to FIG. 3.

Figure 3:
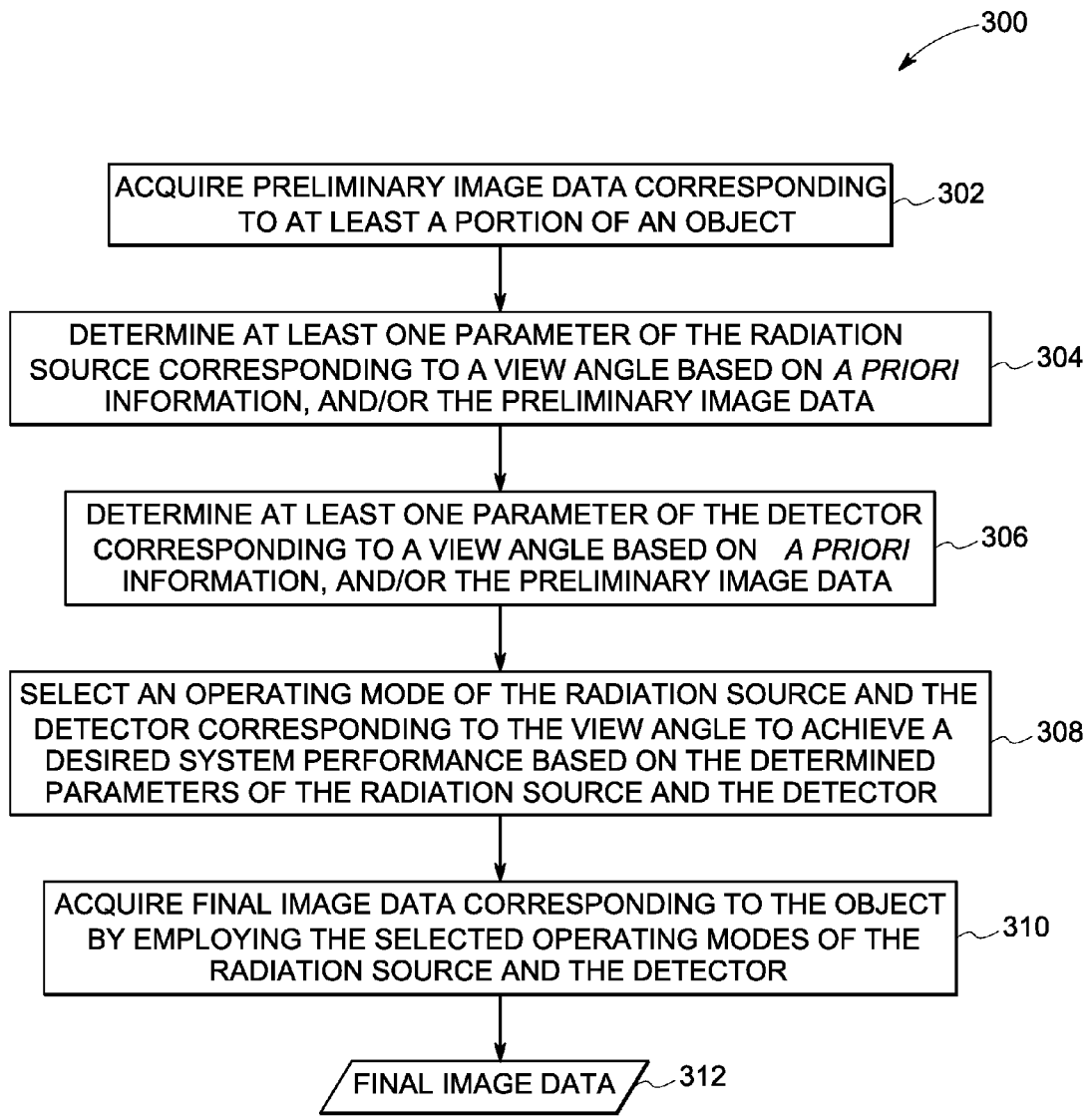
FIG. 3 is a flowchart depicting an exemplary method for acquiring image data, in accordance with aspects of the present technique.

Turning to FIG. 3, a flowchart 300 depicting an exemplary method for acquiring desired image data corresponding to an object, such as the object 204 (see FIG. 2), in an imaging system, such as the CT imaging system 200 of FIG. 2, is illustrated. The method may be described in a general context of computer executable instructions that may be located in either or both of local and remote computer storage media, including memory storage devices. Further, in FIG. 3, the method is illustrated as a collection of blocks in a logical flow graph, which represents a sequence of operations that may be implemented in hardware, software, or combinations thereof. The various operations are depicted in the blocks to illustrate the functions that are performed generally during preliminary data acquisition, selection of desired operating modes of the radiation source and the detector elements, and final image data acquisition phases. In the context of software, the blocks represent computer instructions that, when executed by one or more image processors, perform the recited operations. The order in which the method is described is not intended to be construed as a limitation, and any number of the described blocks may be combined in any order to implement the method disclosed herein, or an equivalent alternative method. Additionally, individual blocks may be deleted from the method without departing from the spirit and scope of the subject matter described herein.

The method begins at step 302, where preliminary image data corresponding to at least a portion of the object may be acquired. As previously noted, the preliminary image data may include, for example, parameters of the object such as object structure, thickness, eccentricity, density, mass, or combinations thereof. In one embodiment, the preliminary image data may further include system parameters. By way of example, the system parameters may include pile up behavior of a detector, such as the detector 108 of FIG. 2, and one or more operating parameters corresponding to a radiation source, such as the radiation source 104 of FIG. 2. The preliminary image data may be acquired, for example, by using a scout scan to obtain anatomical data, through user input, or a combination thereof. Moreover, in certain embodiments, the anatomical data may be evaluated and combined to determine the object parameters, whereas system parameters such as type of imaging required, mA and kVp values, and desired quality of the final image may be input by the user.

Once the preliminary image data is acquired, a desired parameter of the radiation source corresponding to a particular view angle may be determined as indicated by step 304. To that end, the acquired preliminary image data along with a priori information may be evaluated for determining the desired parameter. As previously noted, the a priori information may include a correlation between a determined flux rate in the detector corresponding to a particular view angle of the radiation source and the voltage and the current configuration corresponding to the radiation source. The result of this evaluation may determine an anticipated flux level corresponding to a particular portion of the object acquired at a particular view angle. Accordingly, the acquisition sequence and the operating parameters of the radiation source may be controlled to acquire desired image data.

By way of example, if the acquired preliminary image data corresponds to a thick portion of the object, the desired operating parameters of the radiation source 104 may be determined to include a high kVp and a high mA. Alternatively, if the preliminary image data corresponds to a thin portion of the object, the desired operating parameters of the radiation source 104 may be determined to include a low kVp and a low mA. Further, in some embodiments, multiple radiation sources may be employed to illuminate different portions of the object. In accordance with aspects of the present technique, each of the multiple radiation sources may be operated independently at a different mA, a different kVp, or a combination thereof, to acquire image data corresponding to a desired portion of the object. Thus, the detector may be operated in different operating modes based on different operating parameters determined for different view angles.

Similarly, at step 306, a desired parameter of the detector corresponding to a particular view angle of the radiation source may be determined. As previously noted, the desired parameter of the detector may be determined based on the acquired preliminary image data and the a priori information. In such a scenario, the preliminary image data may also correspond to, for example, a number of energy bins and corresponding thresholds, and available counting modes associated with the detector. In one embodiment, the preliminary image data such as the object and the system parameters, and the desired system performance values may be stored in a data repository communicatively coupled to the imaging system. The desired system performance values stored in the data repository may include, for example, a desired DQE, a desired noise level, a determined limit of a radiation dose transmitted to the object, or combinations thereof. The data repository may also store a previously determined correlation between a determined flux rate in the detector corresponding to a particular view angle of the radiation source and the corresponding kVp and mA values. Based on an evaluation of the stored data, one or more desired parameters corresponding to the detector may be determined. Further, at step 308, based on the desired parameters determined for the radiation source and the detector, desired operating modes associated with the radiation source and the detector and corresponding to a particular view angle may be selected. In one embodiment, the selection of the desired operating mode may be based on a model of the imaging system. By way of example, the model of the imaging system may aim to establish the highest DQE and the lowest noise parameters to be used for any view angle of the radiation source within the constraints of a total radiation dose limit that may be applied to the object.

Subsequently, final image data corresponding to at least the portion of the object may be acquired using the selected operating modes corresponding to the radiation source and the detector as indicated by step 310. The final image data may be used reconstruct a high quality image. A method for reconstructing a high quality image by employing the acquired final image data will be described in greater detail with reference to FIG. 4.

Figure 4:
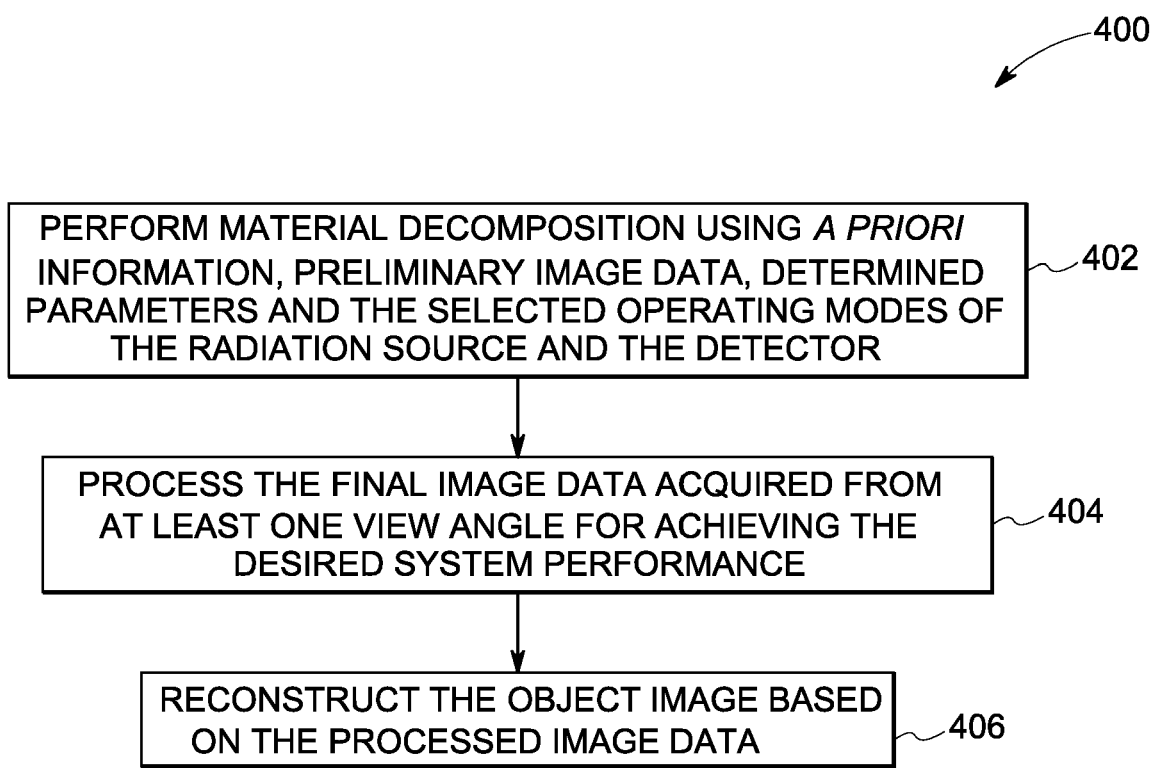
FIG. 4 is a flowchart depicting an exemplary method for reconstructing an image using the image data acquired by employing the exemplary method described with reference to FIG. 3.

Referring now to FIG. 4, a flowchart 400 depicting an exemplary method for reconstructing an image employing the final image data acquired using the exemplary method described with reference to FIG. 3 is presented. To that end, at step 402, material decomposition of the object may be performed. Particularly, in one embodiment, the material decomposition may be based on the preliminary image data acquired at step 302 of FIG. 3, a priori information, determined parameters and the selected operating modes of the radiation source and the detector determined using the exemplary method described with reference to FIG. 3. Moreover, the material decomposition of the object may facilitate evaluation of specific conditions and parameters used to acquire image data corresponding to relevant portions of the object.

Further, at step 404, the data acquired from a plurality of view angles may be processed to obtain relevant information for a good quality reconstruction. Particularly, the effect of the acquired system parameters such as pile-up behavior of the detector may be accounted for while performing material decomposition and image reconstruction. Additionally, one or more criteria for selecting the desired operating modes of the detector and the radiation source, such as the radiation source 102, may also be evaluated during image reconstruction. By way of example, if imaging data corresponding to one view is acquired at a low mA, while imaging data corresponding to another view is acquired at a high mA, the reconstruction algorithm may perform a pre-correction of the acquired data to accommodate differences in the determined parameters corresponding to the different views. Furthermore, the noise introduced across the different views due to the changing thickness of the imaged regions of the object may be minimized by equalizing the noise corresponding to each view. To that end, each of these views may be combined into a final image. Additionally, the noise from each view may be added in quadrature, thereby equalizing the noise across all the views to generate a final image with minimal noise. The pre-correction thus generates processed image data that may be used to reconstruct the final image of the object.

As the processed image data provides information about detector limitations, acquired preliminary image data, selected operating modes, and so on, sufficient and relevant information for reconstructing the object image may be obtained. Therefore, at step 406, the processed image data may be used to provide sufficient information to a reconstruction unit, such as the image reconstructor 230 of FIG. 2, for reconstruction of a high quality image of the object. It may be noted that the processed image data corresponding to the low mA view may be utilized to provide information corresponding to regions that conventionally experience detector saturation. Alternatively, the processed image data corresponding to the high mA view may be used primarily for reconstructing the object image. Particularly, in one embodiment, the image data corresponding to one or more energy bins associated with the PC detector in at least one view may be used to reconstruct a basis set image of the object. Alternatively, the basis set may be calculated for each view by combining energy bin data for the particular view with image data corresponding to adjacent views having different kVps. In general, the basis set for each view may be calculated using information corresponding to all available energy bins corresponding to the detector for a current and neighboring views.

The exemplary system and method disclosed hereinabove, therefore, disclose an efficient technique for acquiring image data for facilitating a high quality reconstruction of an image of an object. To that end, the exemplary system couples fast switching of kVp and mA control of one or more radiation sources with desired configurations of the detector and the radiation source. The desired configurations corresponding to different view angles of the radiation source facilitate acquisition of sufficient imaging data even from conventionally saturated regions, thereby enabling efficient reconstruction of different portions of the object. Particularly, the exemplary system may determine a desired value of flux corresponding to each portion of the object by employing a preliminary scan. Based on a stored correlation between parameters of the radiation source and the detector for different flux rates, the system may select the desired operating modes for the radiation source and the detector to acquire imaging data corresponding to a particular portion of the object. The operating modes may be selected such that at least one of the PC or EI data is available in the region of acquisition. Such predictive selection of the operating modes facilitates faster scanning and efficient material discrimination capability even with lower doses of radiation.

The disclosed technique, thus, may substantially overcome flux rate limitations of conventional PC detectors. In addition, the system may ensure acquisition of sufficient and relevant data from a plurality of view angles by employing multiple source spots that could be fired from different locations. Therefore, the disclosed technique may enable efficient configuration of detector settings for imaging coronary vessels in a lung field where both high flux and low flux regions are encountered at the detector at proximal locations and in rapid succession in time. In certain embodiments, the disclosed technique may also be used to control filtration disposed in the system to achieve improved imaging. The filtration may correspond to one or more material layers placed in between the source and the object for shaping an X-ray energy spectrum. By way of example, one or more layers of copper may be used as filtration to remove low energy photons from an X-ray beam before reaching the object. Thus, by combining rapid control of source mA and kVp, and filtration with configurable detector readout capable of both EI and multi-bin PC, the system may ensure artifact free spectral imaging.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. In an imaging system comprising at least one radiation source and a detector responsive to radiation received from the radiation source, a method for acquiring image data comprising:
   acquiring preliminary image data corresponding to at least a portion of an object;
   determining at least one parameter associated with the radiation source corresponding to a view angle of the radiation source and based on a priori information, the preliminary image data, or a combination thereof;
   determining at least one parameter associated with the detector corresponding to the view angle of the radiation source and based on the a priori information, the preliminary image data, or a combination thereof;
   selecting an operating mode of the radiation source and an operating mode of the detector corresponding to the view angle of the radiation source to achieve a desired system performance, wherein selecting the operating modes corresponding to the radiation source and the detector is based on the determined parameter associated with the radiation source and the determined parameter associated with the detector; and
   acquiring final image data corresponding to at least the portion of the object using the selected operating mode of the radiation source and the selected operating mode of the detector.

2. The method of claim 1, wherein acquiring preliminary image data comprises acquiring one or more structural parameters corresponding to the object.

3. The method of claim 2, wherein the structural parameters comprise a thickness, eccentricity, a density, a mass, or combinations thereof.

4. The method of claim 1, wherein preliminary image data comprises user-defined operating parameters.

5. The method of claim 4, wherein the user-defined operating parameters comprise a voltage (kVp) configuration corresponding to the radiation source, a current (mA) configuration corresponding to the radiation source, a type of imaging, a desired image quality, or combinations thereof.

6. The method of claim 1, wherein the a priori information comprises a correlation between one or more previously determined parameters associated with the radiation source and one or more previously determined parameters associated with the detector corresponding to the view angle of the radiation source.

7. The method of claim 1, wherein the desired system performance comprises a desired detector quantum efficiency, a desired noise level, or a combination thereof.

8. The method of claim 1, wherein the determined parameter associated with the detector comprises a count of corresponding energy bins, a corresponding energy bin threshold, a pile-up behavior of the detector, a flux in the detector corresponding to the view angle of the radiation source, or combinations thereof.

9. The method of claim 1, wherein selecting the operating mode of the detector comprises:
   determining a flux in the detector corresponding to the view angle of the radiation source; and
   switching the detector between a photon counting mode, an energy integration mode, or a combination thereof based on the determined flux.

10. The method of claim 9, wherein switching the detector comprises:
    selecting the photon counting mode for acquiring image data corresponding to a relatively highly attenuating portion of the object; and
    selecting the energy integration mode for acquiring image data corresponding to a relatively less attenuating portion of the object.

11. The method of claim 1, wherein the determined parameter of the radiation source comprises a view angle, a voltage configuration, a current configuration, or combinations thereof.

12. The method of claim 1, wherein selecting the operating mode of the radiation source comprises fast switching of the radiation source between a high voltage configuration, a low voltage configuration, a high current configuration, a low current configuration, or combinations thereof.

13. The method of claim 12, wherein fast switching of the radiation source comprises:
    selecting the high voltage configuration and the high current configuration for acquiring image data from a relatively highly attenuating portion of the object; and
    selecting the low voltage configuration and the low current configuration for acquiring image data corresponding to a relatively less attenuating portion of the object.

14. The method of claim 12, wherein fast switching of the radiation source further comprises selecting the high voltage configuration in one view and the low voltage configuration in adjacent views such that flux in the detector corresponds to a high detector quantum efficiency (DQE) operation in a photon counting mode for acquiring image data corresponding to the relatively highly attenuating portion of the object.

15. The method of claim 1, further comprising reconstructing a basis set image of the object based on energy data corresponding to a plurality of energy bins associated with the detector in a current and adjacent views.

16. The method of claim 1, further comprising reconstructing an image of the object based on the final image data.

17. The method of claim 16, wherein reconstructing the image comprises:
    performing material decomposition of at least the portion of the object based on the a priori information, the preliminary image data, the determined parameter of the radiation source, the determined parameter of the detector, the selected operating mode of the detector, the selected operating mode of the radiation source, or combinations thereof;

processing the final image data corresponding to at least one view angle of the radiation source to achieve the desired system performance to generate processed image data; and reconstructing the image of the object using the processed image data.

18. An imaging system, comprising:
at least one radiation source that emits radiation towards an object;
a detector that receives the radiation from the radiation source;
a data acquisition system (DAS) that:
   acquires preliminary image data corresponding to at least a portion of the object;
   determines at least one parameter associated with the radiation source corresponding to a view angle of the radiation source and based on a priori information, the preliminary image data, or a combination thereof;
   determines at least one parameter associated with the detector corresponding to the view angle of the radiation source and based on the a priori information, the preliminary image data, or a combination thereof; and
an adaptive controller that selects an operating mode of the radiation source and an operating mode of the detector corresponding to the view angle of the radiation source to achieve a desired system performance based on the determined parameter associated with the radiation source and the determined parameter associated with the detector.

19. The imaging system of claim 18, wherein the DAS further acquires final image data corresponding to at least the portion of the object using the selected operating mode of the radiation source and the selected operating mode of the detector.

20. The imaging system of claim 18, further comprising a data repository that stores the a priori information, the preliminary image data, the determined parameter of the radiation source, the determined parameter of the detector, the selected operating mode of the detector, the selected operating mode of the radiation source, or combinations thereof.

21. The imaging system of claim 18, wherein the data acquisition system comprises a computer tomography (CT) system, a positron emission tomography (PET) scanner, a single photon emission computed tomography (SPECT) scanner, a baggage screening system, or combinations thereof.

22. The imaging system of claim 18, wherein the adaptive controller determines a flux in the detector corresponding to the view angle of the radiation source.

23. The imaging system of claim 22, wherein the adaptive controller switches the detector between a photon counting mode, an energy discrimination mode, or a combination thereof based on the determined flux.

24. The imaging system of claim 23, wherein the adaptive controller switches the detector to the photon counting mode to acquire image data corresponding to a relatively highly attenuating portion of the object and switches the detector to the energy integration mode for acquiring image data corresponding to a relatively less attenuating portion of the object.

25. The imaging system of claim 24, wherein the adaptive controller performs fast switching of the radiation source between a high voltage configuration, a low voltage configuration, a high current configuration, a low current configuration, or combinations thereof.

26. The imaging system of claim 25, wherein the adaptive controller selects the high voltage configuration and the high current configuration as a desired operating mode of the radiation source for acquiring image data corresponding to the relatively highly attenuating portion of the object and selects the low voltage configuration and the low current configuration as a desired operating mode of the radiation source for acquiring image data corresponding to the relatively less attenuating portion of the object.

27. The imaging system of claim 25, wherein the adaptive controller selects the high voltage configuration in one view and the low voltage configuration in adjacent views such that flux in the detector corresponds to a high detector quantum efficiency (DQE) operation in a photon counting mode for acquiring image data from a relatively highly attenuating portion of the object.

28. The imaging system of claim 18, further comprising an image reconstruction unit for reconstructing a basis set image of the object based on data available from one or more energy bins associated with the detector corresponding to a current view and adjacent views.

29. The imaging system of claim 18, further comprising an image reconstruction unit for reconstructing an image of the object based on the final image data.

30. The imaging system of claim 29, wherein the image reconstruction unit:
performs material decomposition of at least the portion of the object based on the a priori information, the preliminary image data, the determined parameter associated with the radiation source, the determined parameter associated with the detector, the selected operating mode of the detector, the selected operating mode of the radiation source, or combinations thereof;
processes the final image data corresponding to at least one view angle of the radiation source to achieve the desired system performance to generate processed image data; and
reconstructs the object image using the processed image data.

31. A computer tomography (CT) system, comprising:
a rotatable gantry having an opening to receive an object to be scanned;
at least one radiation source operatively coupled to the rotatable gantry and that emits radiation towards the object;
a detector that receives the radiation from the radiation source; and
a computing device that:
   acquires preliminary image data corresponding to at least a portion of an object;
   determines at least one parameter associated with the radiation source corresponding to a view angle of the radiation source and based on a priori information, the preliminary image data, or a combination thereof;
   determines at least one parameter associated with the detector corresponding to the view angle of the radiation source and based on the a priori information, the preliminary image data, or a combination thereof;
   selects an operating mode of the radiation source and an operating mode of the detector corresponding to the view angle of the radiation source to achieve a desired system performance, wherein the operating modes corresponding to the radiation source and the detector are selected based on the determined parameter associated with the radiation source and the determined parameter associated with the detector; and acquires final image data corresponding to at least the portion of the object using the selected operating mode of the radiation source and the selected operating mode of the detector.

32. The CT system of claim 31, further comprising a data repository for storing the a priori information, the preliminary image data, the determined parameter associated with the radiation source, the determined parameter associated with the detector, the selected operating mode of the detector, the selected operating mode of the radiation source, or combinations thereof.

33. The CT system of claim 31, further comprising an image reconstruction unit for reconstructing an image of the object using the final image data, material decomposition information corresponding to the object, one or more criteria for selection of the operating modes of the radiation source and the detector, or combinations thereof.

* * * * *